(12) United States Patent
Takei et al.

(10) Patent No.: US 8,721,532 B2
(45) Date of Patent: May 13, 2014

(54) ENDOSCOPE APPARATUS AND METHOD FOR CONTROLLING FLUORESCENCE IMAGING APPARATUS

(71) Applicant: Olympus Medical Systems Corp., Tokyo (JP)

(72) Inventors: Shunji Takei, Hachioji (JP); Nobuyuki Doguchi, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/708,149

(22) Filed: Dec. 7, 2012

(65) Prior Publication Data
US 2013/0096376 A1    Apr. 18, 2013

Related U.S. Application Data

(63) Continuation of application No. PCT/JP2012/058968, filed on Apr. 2, 2012.

(30) Foreign Application Priority Data

Jun. 7, 2011    (JP) ................................. 2011-127566

(51) Int. Cl.
*A61B 1/06* (2006.01)
*A61B 1/04* (2006.01)

(52) U.S. Cl.
USPC ........................... 600/180; 600/109; 600/160

(58) Field of Classification Search
USPC .......... 600/160, 109, 117, 118, 178–181, 476
See application file for complete search history.

(56) References Cited

U.S. PATENT DOCUMENTS

| 6,371,908 | B1 | 4/2002 | Furusawa et al. |
| 6,492,646 | B1 | 12/2002 | Sendai et al. |
| 6,760,058 | B2 * | 7/2004 | Hakamata ....................... 348/45 |
| 6,962,565 | B2 * | 11/2005 | Nakamura .................... 600/179 |
| 7,123,756 | B2 * | 10/2006 | Hakamata et al. ............. 382/128 |
| 7,283,858 | B2 * | 10/2007 | Sendai .......................... 600/407 |
| 7,667,180 | B2 * | 2/2010 | Maeda ........................ 250/208.1 |
| 8,212,892 | B2 * | 7/2012 | Yamazaki .................. 348/229.1 |

(Continued)

FOREIGN PATENT DOCUMENTS

| EP | 1 089 067 A2 | 4/2001 |
| EP | 2 123 213 A2 | 11/2009 |

(Continued)

*Primary Examiner* — Philip R Smith
*Assistant Examiner* — William Chou
(74) *Attorney, Agent, or Firm* — Scully, Scott, Murphy & Presser, P.C.

(57) ABSTRACT

An endoscope apparatus includes: a light source portion that irradiates an excitation light and a reference light alternately; an image pickup portion that picks up images of the fluorescence from the living tissue and the reflected light; a signal processing portion that generates image signals from picked up signals; an addition processing portion that generates, from image signals of fluorescence, addition processed signals of fluorescence in which pixels are added; a light quantity control portion that controls the quantity of light so as to maintain a predetermined light quantity ratio between the quantities of the excitation light and the reference light from the addition processed signals of fluorescence and image signals of the reflected light; and a superimposition processing portion that superimposes the addition processed signals and the image signals of the reflected light, with the predetermined light quantity ratio being maintained.

16 Claims, 12 Drawing Sheets

(56) References Cited

U.S. PATENT DOCUMENTS

| | | | |
|---|---|---|---|
| 8,498,695 B2 * | 7/2013 | Westwick et al. | 600/478 |
| 2002/0035330 A1 * | 3/2002 | Cline et al. | 600/476 |
| 2004/0210107 A1 * | 10/2004 | Tani et al. | 600/109 |
| 2009/0289200 A1 | 11/2009 | Ishii | |
| 2010/0210904 A1 * | 8/2010 | Cline et al. | 600/109 |

FOREIGN PATENT DOCUMENTS

| | | |
|---|---|---|
| JP | 01-212077 A | 8/1989 |
| JP | 2000-023903 A | 1/2000 |
| JP | 2001-161696 A | 6/2001 |
| JP | 2008-259595 A | 10/2008 |
| JP | 2009-178180 A | 8/2009 |
| JP | 2009-279172 | 12/2009 |

* cited by examiner

FIG. 2
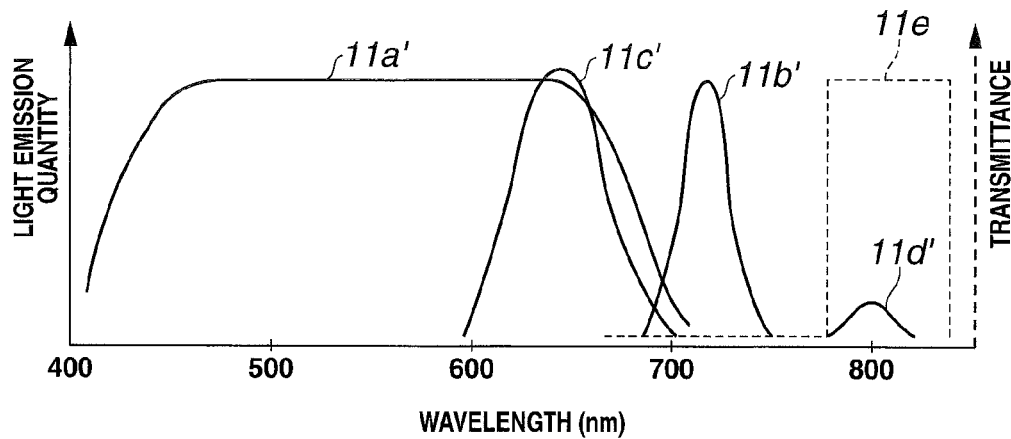
FIG. 3
(A)
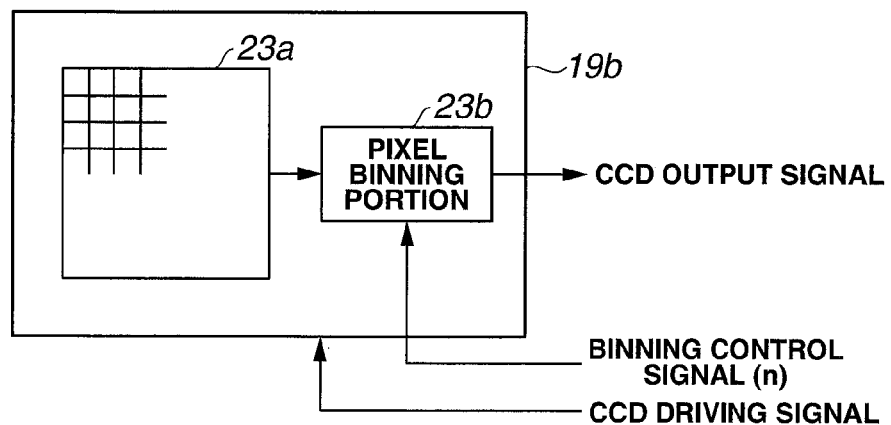
(B)
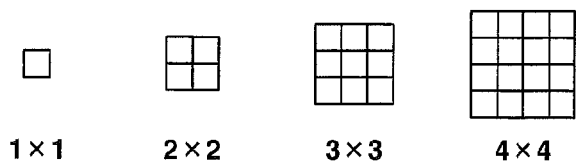

FIG.4
(A)
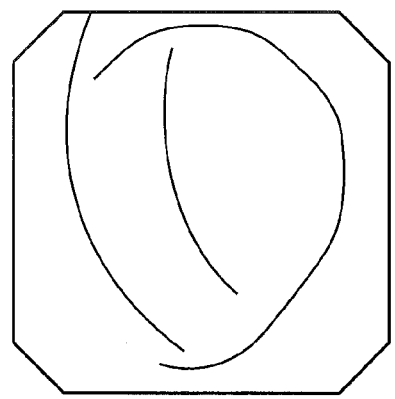
(B)
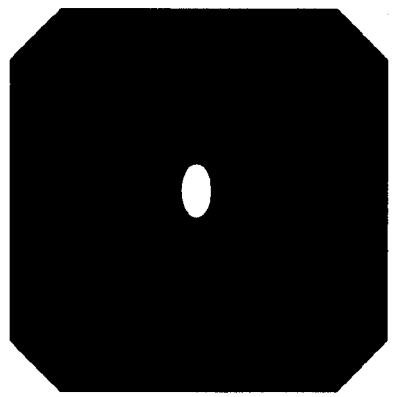
(C)
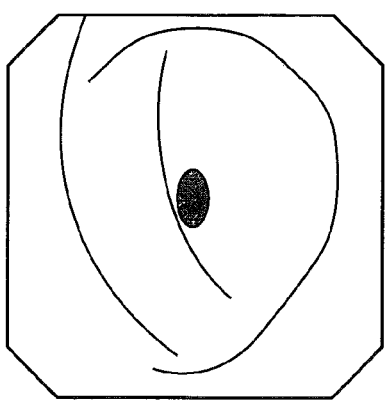

| MEMORY ADDRESS | LED DRIVING CURRENT [mA] | QUANTITY OF ILLUMINATING LIGHT FROM EXCITATION LIGHT LED [mW] |
|---|---|---|
| XXX10010 | 100 | 10 |
| XXX10020 | 101 | 10.2 |
| ..... | ... | ... |
| ..... | ... | ... |
| XXX10100 | 200 | 23 |
| ..... | ... | ... |

(B)

| MEMORY ADDRESS | LED DRIVING CURRENT [mA] | QUANTITY OF ILLUMINATING LIGHT FROM REFERENCE LIGHT LED [mW] |
|---|---|---|
| XXX20001 | 10 | 2 |
| XXX20002 | 10.1 | 2.1 |
| ..... | ... | ... |
| ..... | ... | ... |
| XXX20100 | 20 | 4.3 |
| ..... | ... | ... |

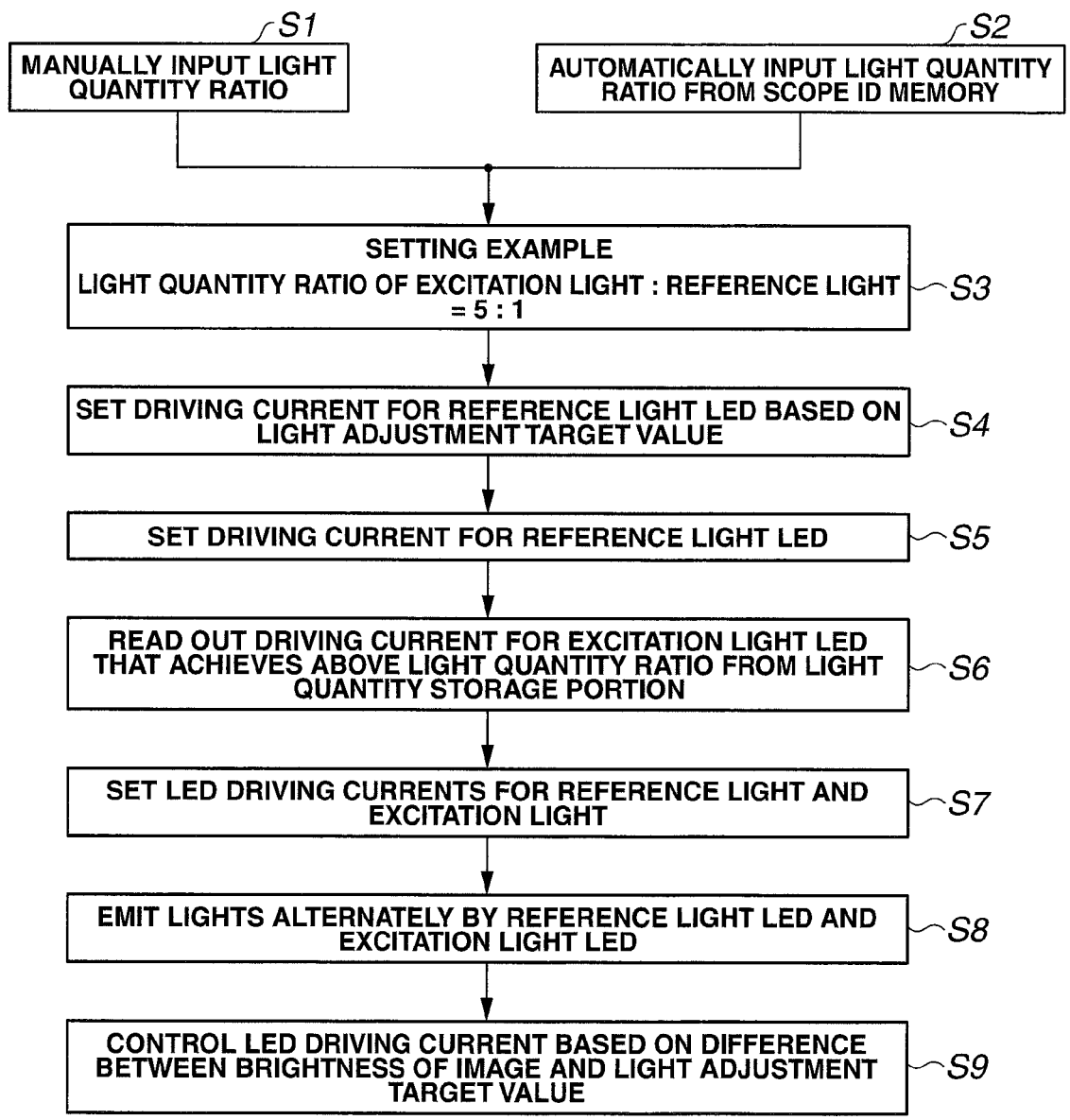

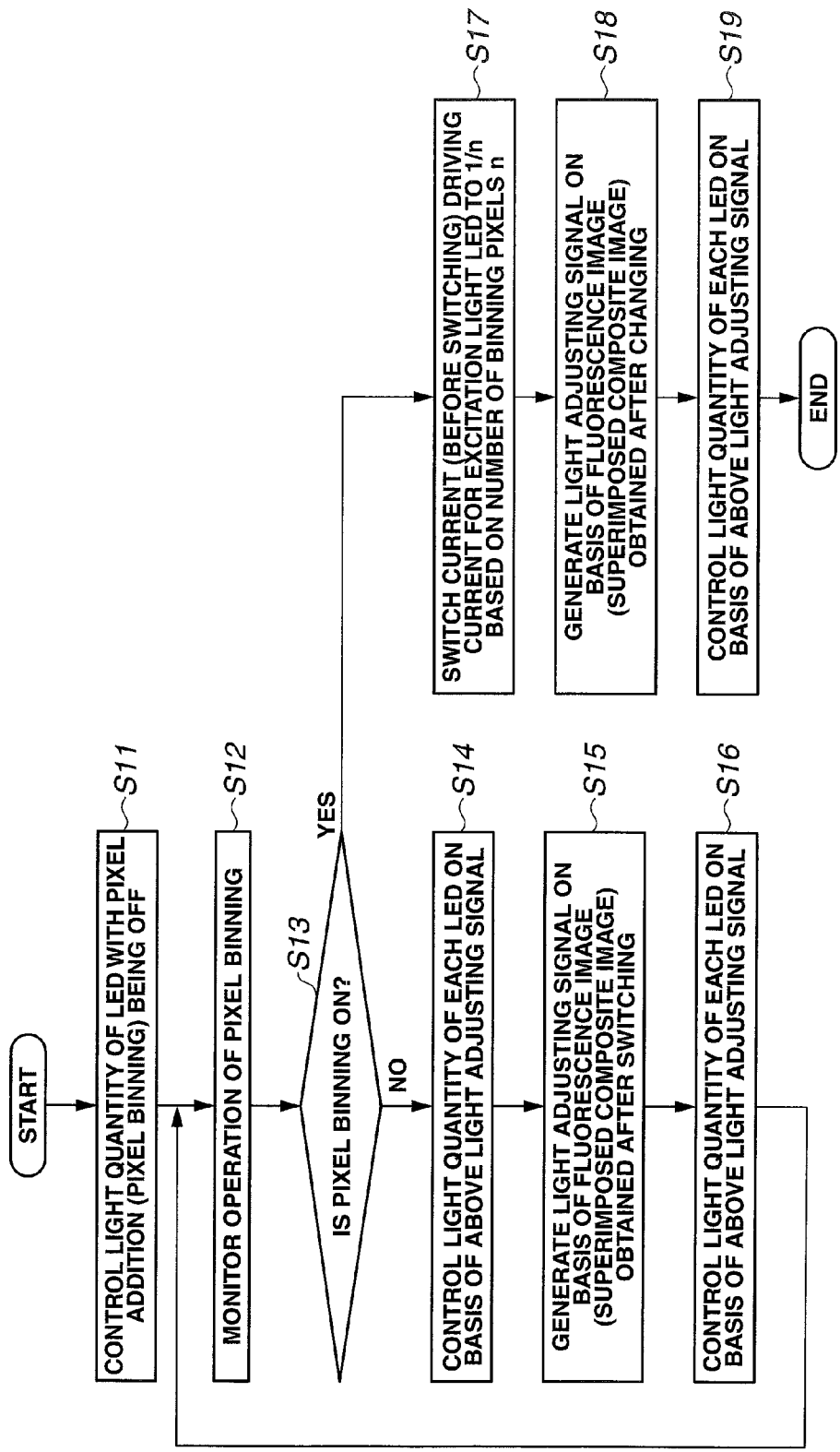

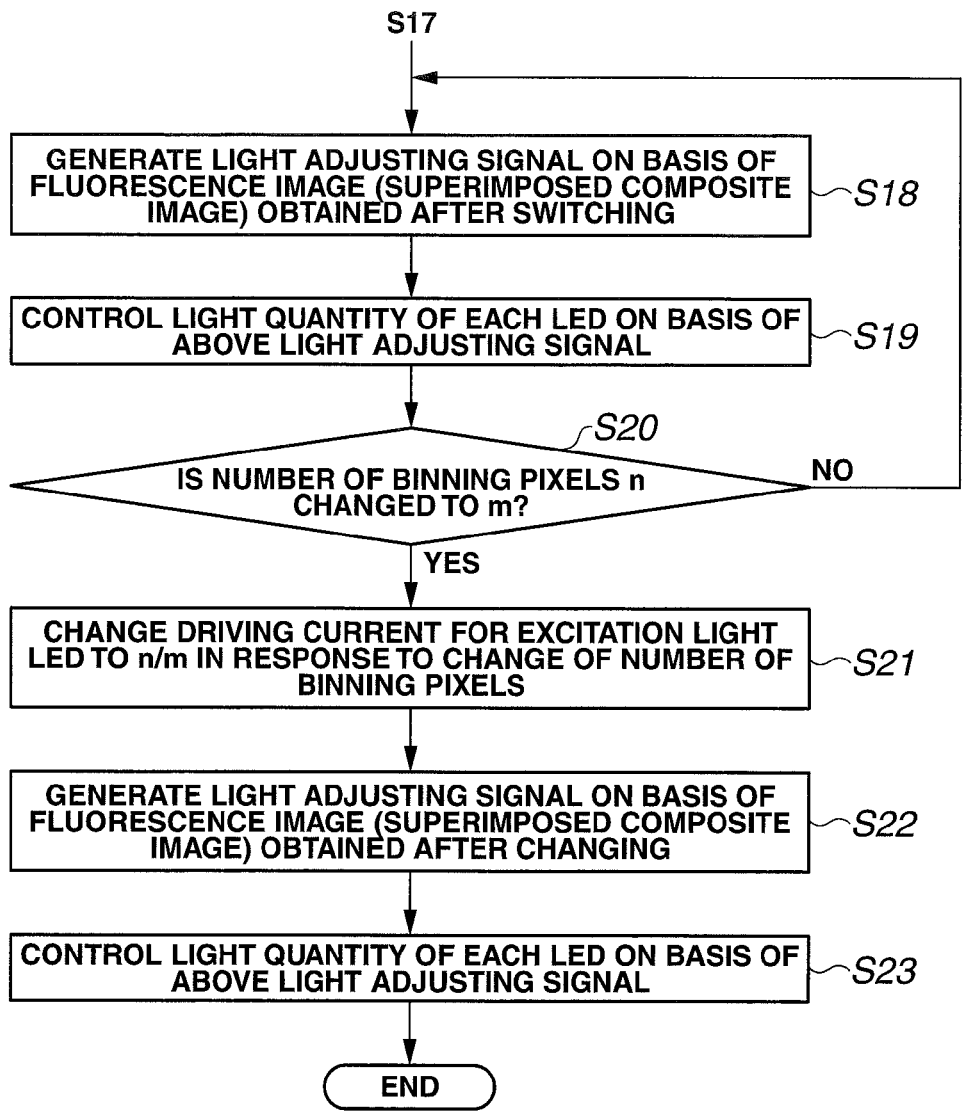

ENDOSCOPE APPARATUS AND METHOD FOR CONTROLLING FLUORESCENCE IMAGING APPARATUS

CROSS REFERENCE TO RELATED APPLICATION

This application is a continuation application of PCT/JP2012/058968 filed on Apr. 2, 2012 and claims benefit of Japanese Application No. 2011-127566 filed in Japan on Jun. 7, 2011, the entire contents of which are incorporated herein by this reference.

BACKGROUND OF THE INVENTION

1. Field of the Invention

The present invention relates to an endoscope apparatus that performs fluorescence imaging and a method for controlling a fluorescence imaging apparatus.

2. Description of the Related Art

An endoscope apparatus which uses an endoscope has been widely used in a medical field. A light source apparatus of a conventional endoscope has generally adopted a scheme to attain the irradiation with a desired light from a white color light source such as a xenon lamp and a halogen lamp through a band-pass filter.

In recent years, inexpensive and high-output solid light-emitting devices such as a light emitting diode (abbreviated as LED) and a semiconductor laser have been put into practical use, and a light source apparatus or an illuminating apparatus made of a combination of a plurality of light-emitting devices, for an endoscope, has been used.

Such a light source apparatus can advantageously control a quantity of light for each wavelength independently. However, disadvantageously, in the case where an image is obtained or generated by means of illumination by a plurality of light-emitting devices, or a plurality of images are displayed superimposed on one another, if a light quantity ratio of the plurality of light-emitting devices is not controlled to be constant, the balance and the like of an obtained image may be distorted.

In particular, in the case where an image of fluorescence (a fluorescence image) and an image of a reflected light of a reference light (a reflected image) are superimposed on one another or the like to display the images at the same time, if the intensities of both the images are substantially different, it is also desired that the light quantity ratio be controlled to be constant.

In order to address such a case, for example, in a conventional example disclosed in Japanese Patent Application Laid-Open Publication No. 2008-259595, an intensity control portion controls a relative intensity of illuminating light components with respect to excitation light components depending on the luminance value of observation image data from a fluorescence image and a reflected image of a subject, and adjusts the balance of the reflected image with respect to the fluorescence image.

SUMMARY OF THE INVENTION

An endoscope apparatus according to an aspect of the present invention includes: a light source portion including light sources that irradiate living tissue with an excitation light for generating fluorescence and a reference light for generating a reflected light alternately; an image pickup portion including image pickup devices having a predetermined number of pixels for picking up images of the fluorescence generated by the irradiation of the living tissue with the excitation light and a reflected light of the reference light reflected by the living tissue; a signal processing portion that generates image signals from signals picked up by the image pickup portion; an addition processing portion that generates, from fluorescence signals obtained when the image of the fluorescence is picked up or the image signals of the fluorescence generated by the signal processing portion, addition processed signals of fluorescence in which a plurality of adjacent pixels are added; a light quantity control portion that controls a quantity of at least one of the excitation light and the reference light so as to maintain a predetermined light quantity ratio between quantities of the excitation light and the reference light from the addition processed signals of the fluorescence and reflected light signals as the image signals of the reflected light on the basis of change in a number of pixels to be added in the addition processing portion; and a superimposition processing portion that outputs, to a display portion, superimposed image signals in which the addition processed signals of the fluorescence and the reflected light signals are superimposed, with the predetermined light quantity ratio being maintained in the light quantity control portion.

A method for controlling a fluorescence imaging apparatus according to an aspect of the present invention includes: a signal processing step in which a signal processing portion generates image signals from obtained fluorescence signals and reflected light signals reflected by living tissue; a pixel addition processing step in which a pixel addition processing portion generates addition processed signals of fluorescence obtained by addition processing among a plurality of adjacent pixels from the fluorescence signals or the image signals of the fluorescence generated in the signal processing step; a light adjusting signal generating step in which, a light adjusting signal generating portion generates a light adjusting signal for controlling a quantity of at least one of the excitation light and the reference light by a light quantity control portion so as to maintain a predetermined light quantity ratio between quantities of the excitation light and the reference light from the addition processed signals of the fluorescence and reflected light signals as the image signals of the reflected light on the basis of change in the number of pixels to be added in the pixel addition processing step; and a superimposition signal generating step in which a superimposition processing portion generates superimposed image signals in which the addition processed signals of the fluorescence and the reflected light signals are superimposed, with the predetermined light quantity ratio being maintained in the light adjusting signal generating step.

BRIEF DESCRIPTION OF THE DRAWINGS

FIG. 2 is a diagram showing a wavelength range within which a white color light LED emits light or the like;

FIG. 3 is an explanatory diagram of an addition processing portion provided in an image pickup device for fluorescence imaging;

FIG. 4 is a diagram showing an example of a composite image that is a superimposition image of a reflected light image and a fluorescence image and displayed on a monitor;

FIG. 5 is a diagram showing specific examples of information stored in a light quantity storage portion;

FIG. 6B is an explanatory diagram showing the operation of a light-adjusting circuit driving respective LEDs of a light source apparatus with a light quantity ratio set by a light quantity ratio setting portion through an LED driving circuit;

FIG. 7 is a flow chart showing an operation of light quantity control for the LEDs when pixel addition is switched from an OFF state to an ON state;

FIG. 8 is a flow chart showing an operation of light quantity control for the LEDs when the number of binning pixels to be added is changed (switched);

FIG. 9A is a block diagram showing a configuration in which an upper-limit value of an LED driving current is inputted to the light-adjusting circuit as a threshold;

DETAILED DESCRIPTION OF THE PREFERRED EMBODIMENTS

Embodiments of the present invention will now be described with reference to the drawings.

First Embodiment

Figure 1:
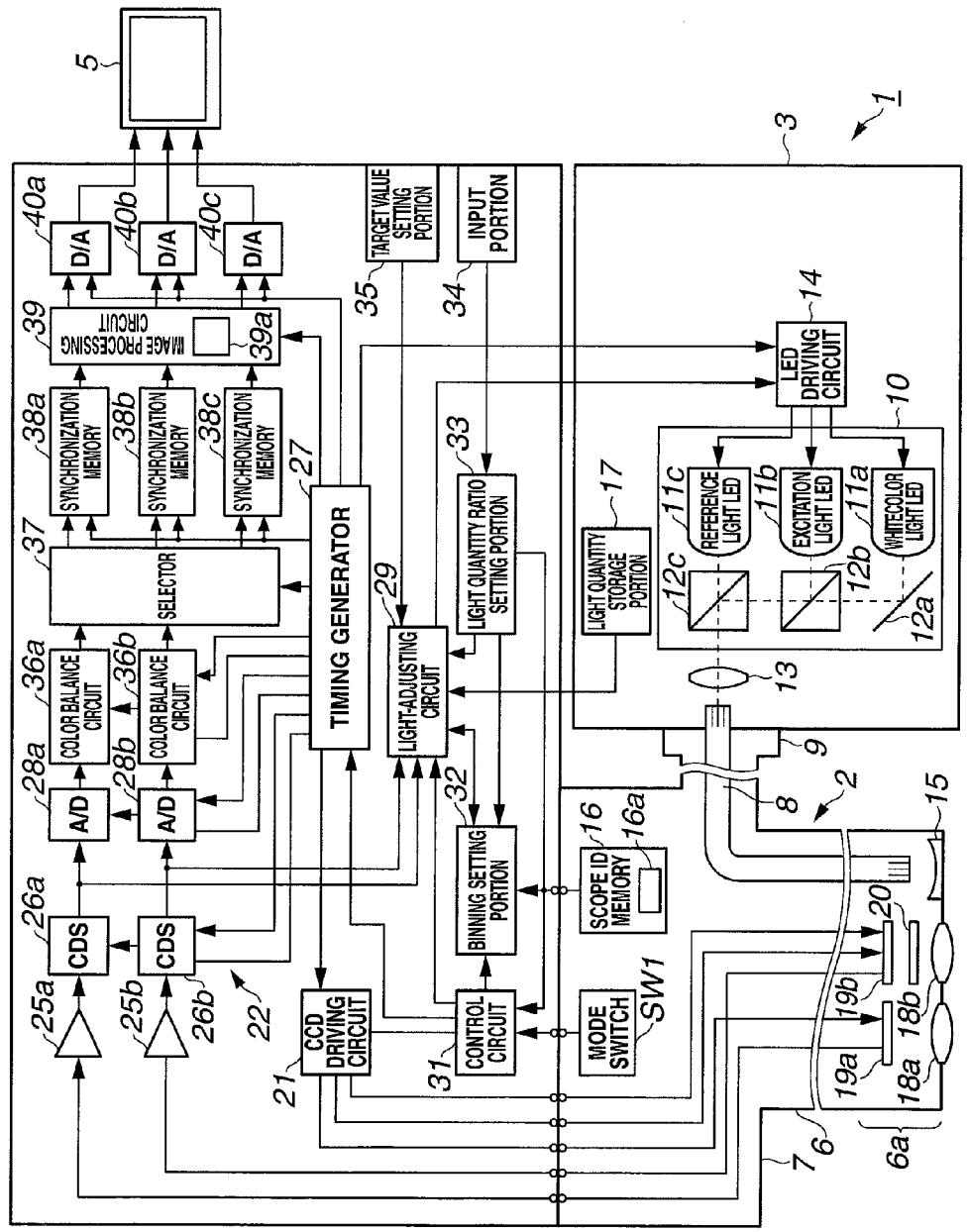
FIG. 1 is a diagram showing an entire configuration of an endoscope apparatus according to a first embodiment of the present invention.

As shown in FIG. 1, an endoscope apparatus 1 of the present embodiment includes an electronic endoscope (hereinafter, simply abbreviated as endoscope) 2 having image pickup means that is inserted in a body cavity to pick up an image of tissue in the body cavity, a light source apparatus 3 that includes light sources for supplying the endoscope 2 with illuminating light, a video processor 4 as signal processing means that processes image pickup signals from the image pickup means of the endoscope 2 to generate image signals, and a monitor 5 as a display device that displays the image signals as an endoscope images in response to the input of the signals.

The endoscope 2 includes an elongated insertion portion 6 and an operation portion 7 provided at a rear end side thereof. A light guide connector 9 provided at an incident end portion side of a light guide 8 extended from the operation portion 7 is detachably connected with the light source apparatus 3.

The light source apparatus 3 includes a light source unit 10 that has light sources for each emitting a white color light, an excitation light, and a reference light. The light source unit 10 includes a white color light diode (abbreviated as LED) 11a, an excitation light LED 11b, and a reference light LED 11c as light sources which respectively emit a white color light, an excitation light, and a reference light. The LEDs 11a, 11b, and 11c emit light by driving currents supplied from an LED driving circuit 14. Note that an LED which emits red, green, and blue lights may be substituted for the white color LED 11a.

A white color light emitted by the white color light LED 11a is reflected by a mirror 12a and then transmitted through a first dichroic prism 12b that is an optical device (a selective optical device) for selectively reflecting or transmitting light depending on an incident wavelength. The light (except for the wavelength range of the reference light) is further reflected by a second dichroic prism 12c that is a selective optical device. Thereafter, a condenser lens 13 concentrates the light, which is then incident on the incident end portion of the light guide 8.

An excitation light emitted by the excitation light LED 11b is selectively reflected by the first dichroic prism 12b and further reflected by the second dichroic prism 12c. Thereafter, the condenser lens 13 concentrates the light, which is then incident on the incident end portion of the light guide 8.

A reference light emitted by the reference light LED 11c is selectively transmitted by the second dichroic prism 12c. Thereafter, the condenser lens 13 concentrates the light, which is then incident on the incident end portion of the light guide 8. In addition to the foregoing configuration, the light source unit 10 may be defined as a configuration including the condenser lens 13.

The light guide 8 conveys the light incident on the incident end portion. The light travels via a light guide front end face installed in a distal end portion 6a of the insertion portion 6 to an illumination lens 15 mounted on an illuminating window, and living tissue of a site to be observed in front of the window is irradiated with the light.

The operation portion 7, for example, in the endoscope 2 is provided with a mode switch SW1 which switches or selects an imaging mode. An operator as a user of the endoscope 2 may operate the mode switch SW1 to select a normal-light imaging mode (or a normal imaging mode) in which normal-light imaging (or normal imaging) is performed with the irradiation with a white color light, or a fluorescence imaging mode in which fluorescence imaging is performed with the irradiation with an excitation light.

The endoscope 2 detachably connected with the video processor 4 includes a scope ID memory 16 that stores ID information unique to the endoscope 2, information such as the number of pixels of CCDs 19a and 19b described later, which are mounted in the endoscope 2, and information that specifies use conditions recommended for fluorescence imaging.

The scope ID memory 16 includes a light quantity ratio information storage portion 16a that stores light quantity ratio information which is information on a light quantity ratio (or an intensity ratio) between an excitation light and a reference light recommended if the fluorescence imaging is performed using the endoscope 2 in the fluorescence imaging mode.

In the present embodiment, in the fluorescence imaging mode, the light source apparatus 3 supplies an excitation light and a reference light alternately to the light guide 8, and the living tissue of the site to be observed is irradiated alternately with an excitation light and a reference light. As described later, in accordance with the light quantity ratio information, the light source apparatus 3 generates an excitation light and a reference light with the quantities thereof achieving a predetermined light quantity ratio.

The video processor 4 performs superimposition processing that superimposes fluorescence image signals and image signals of a reflected-light from the irradiation with the reference light, and allows the superimposed endoscope image to be displayed on the monitor 5.

FIG. 4 shows, in the fluorescence imaging mode, a reflected light image (see FIG. 4(A)) corresponding to image signals of a reflected light, a fluorescence image (see FIG.

4(B)) corresponding to fluorescence image signals, and a composite image (see FIG. 4(C)) that is a superimposition image made by superimposing these images on one another in alignment with each other.

In FIG. 2, wavelength ranges of the white color light, the excitation light, and the reference light each generated by the white color light LED 11a, the excitation light LED 11b, and the reference light LED 11c are denoted by reference numerals 11a', 11b', and 11c', respectively. In an example shown in FIG. 2, the reference light corresponds to the wavelength range of red (R), for example, and if the irradiation with the reference light occurs, a CCD 19a obtains the light as R image signals. Note that light emission quantities of the white color light, the excitation light, and the reference light in FIG. 2 indicate exemplary characteristics appearing when the LEDs are driven by the LED driving circuit 14 with LED driving currents having a same value, for example.

Also, in FIG. 2, an exemplary wavelength range of fluorescence described later is denoted by reference numeral 11d'. The intensity of fluorescence radiated or emitted from a medication administered to living tissue is still smaller than the intensity of the excitation light or the like.

The light source apparatus 3 includes a light quantity storage portion 17 that stores information such as information on LED driving currents outputted (to the excitation light LED 11b and the reference light LED 11c) from the LED driving circuit 14 (see FIGS. 5(A) and (B) described later) so as to, in the fluorescence imaging mode, emit the excitation light LED 11b and the reference light LED 11c with a predetermined light quantity ratio between the excitation light and the reference light being maintained.

On the other hand, in the normal imaging mode, the living tissue is irradiated with a white color light. In the configuration of the light source apparatus 3 shown in FIG. 1, a wavelength range of a white color light generated by the white color light LED 11a that is equivalent to a wavelength range of a reference light is dropped by the second dichroic prism 12c, but the living tissue can be irradiated with a white color light by the white color light LED 11a and the reference light LED 11c simultaneously emitting lights.

In this way, in the normal imaging mode, the LED driving circuit 14 drives the white color light LED 11a and the reference light LED 11c simultaneously. A light-adjusting circuit 29 performs light adjustment control to maintain the quantities of the lights from the white color light LED 11a and the reference light LED 11c to be constant through the LED driving circuit 14.

By using the white color light LED 11a and the reference light LED 11c which have, for example, the same characteristics of the LED driving currents and the light emission quantities, in the normal imaging mode, substantially the same LED driving currents may irradiate the living tissue with a white color light balanced to achieve an even light-emission intensity across a visible wavelength range.

In the distal end portion 6a of the insertion portion 6, a normal imaging window (a normal image pickup window) and a fluorescence imaging window (a fluorescence image pickup window) are provided adjacently to the illuminating window. An objective lens 18a is installed in the normal imaging window, and at an image forming position thereof, a charge coupled device (abbreviated as CCD) 19a that forms image pickup means (an image pickup portion) for the normal imaging is installed. An image pickup surface of the CCD 19a is provided with a color filter that separates a light into colors of red (R), green (G), and blue (B) by the pixel, for example.

An objective lens 18b is installed in the fluorescence imaging window, and at an image forming position thereof, a CCD 19b that forms image pickup means for the fluorescence imaging is installed. An excitation light blocking filter 20 that blocks an excitation light is installed between the objective lens 18b and the CCD 19b.

The excitation light blocking filter 20 is set at characteristics 11e (right-hand transmission characteristics) that block the excitation light shown with dotted lines in FIG. 2, and has characteristics that transmit the wavelength range of fluorescence, which is at a longer wavelength range side than the wavelength range of the excitation light.

In response to the application of CCD driving signals to the CCDs 19a and 19b from a CCD driving circuit 21, the CCDs 19a and 19b each output image pickup signals photoelectrically converted by a photoelectric conversion portion (or a light-receiving portion) as output signals. The numbers of pixels in length and width of the CCDs 19a and 19b may be equal to each other or may also be different. The objective optical systems 18a and 18b may have the same characteristics or may also have different characteristics.

Output signals from the CCDs 19a and 19b are inputted to an image signal processing portion 22 in the video processor 4.

As shown in FIG. 3(A), the CCD 19b in the present embodiment includes a pixel binning portion 23b that forms addition processing means for generating addition processed signals of fluorescence in which pixels are added. On the other hand, the CCD 19a is a normal CCD (without a pixel binning portion).

The CCD 19b includes a photoelectric conversion portion (or a light-receiving portion) 23a with a predetermined number of pixels (having a photoelectric conversion function) arranged regularly in a horizontal and a vertical direction at fixed pitched. The CCD 19b also includes the pixel binning portion 23b with a function of outputting a signal of each pixel picked up by the photoelectric conversion portion 23a as an image signal of one pixel without adding the respective pixels unlike a normal CCD, and a function of performing addition processing for a plurality of pixels indicated by the application of a pixel binning control signal (abbreviated as binning control signal) to output a pixel binning image signal that is an addition processed signal as an image signal of one pixel.

If the binning control signal is not applied from the CCD driving circuit 21 (the binning control signal is off), as shown with a leftmost illustration in FIG. 3(B), the pixel binning portion 23b outputs an image signal of one pixel (1×1). Note that i×i (i=1, 2, 3, and so on) indicates that the numbers of pixels in the horizontal and the vertical directions are each i (i is a natural number).

On the other hand, if the binning control signal is applied (the binning control signal is on), the pixel binning portion 23b outputs a pixel binning image signal (abbreviated as binning image signal) that is an addition processed signal in which pixel signals of 2×2, 3×3, and 4×4 pixels are added depending on a level of the binning control signal or the like as shown in FIG. 3(B). In the present embodiment, a binning control signal (n) designates the number of pixels to be added (abbreviated as the number of addition pixels or the number of binning pixels) n, which is n=4, 9, 16, and so on.

Output signals from the CCDs 19a and 19b are amplified by amplifiers 25a and 25b which are part of the image signal processing portion 22 in the video processor 4, and then inputted to correlated double sampling circuits (CDS circuits) 26a and 26b, respectively, where signal components are extracted.

The CCD driving circuit 21 and the CDS circuits 26a and 26b each receive (as input) timing signals from a timing generator 27 that generates timing signals for various types of timing control. The CCD driving circuit 21 and the CDS circuits 26a and 26b each perform sampling in synchronization with the timing signals to extract CCD driving signals and signal components.

Output signals from the CDS circuits 26a and 26b are inputted to A/D converting circuits 28a and 28b and also to a light-adjusting circuit 29 that is light quantity control means. The light-adjusting circuit 29 performs light adjustment control (light quantity control) on the basis of the input signal.

The video processor 4 includes: a control circuit 31 that performs illuminating associated with the imaging mode selected by the operation of the mode switch SW1 and image signal processing; a function of turning on/off the pixel binning if the CCD 19b can carry out the pixel binning from the scope ID memory 16; and a pixel binning setting portion (abbreviated as binning setting portion) 32 that sets the number of binning pixels n for the case where the pixel binning is on.

The video processor 4 further includes a light quantity ratio setting portion 33 that sets a light quantity ratio between the excitation light and the reference light in the fluorescence imaging mode.

The light quantity ratio setting portion 33 receives information on a light quantity ratio from the scope ID memory 16 (as input). The light quantity ratio setting portion 33 may automatically set the light quantity ratio using the information on the light quantity ratio, as well as a light quantity ratio may also be manually set at a rate inputted from an input portion 34. The information on the light quantity ratio set by the light quantity ratio setting portion 33 is sent to the light-adjusting circuit 29.

Also, the light quantity ratio setting portion 33 may be connected with the binning setting portion 32 to set (designate) the number of binning pixels n by the binning setting portion 32. As described later, the present embodiment has a mode in which the light-adjusting circuit 29 variably adjusts the number of binning pixels n automatically, to perform light quantity control.

The control circuit 31 refers to information in the scope ID memory 16 to perform the control for the CCDs 19a and 19b of the endoscope 2 connected with the video processor 4. The control circuit 31 also controls the operation of the timing generator 27, the CCD driving circuit 21, and the light-adjusting circuit 29 depending on the imaging mode.

The control circuit 31 also permits the binning setting portion 32 to set the operation of the pixel binning only if a mode is switched to the fluorescence imaging mode.

In the fluorescence imaging mode, if pixel binning is performed, the binning setting portion 32 outputs information on the number of binning pixels n to the light-adjusting circuit 29 in response to the control by the light-adjusting circuit 29. The light-adjusting circuit 29 controls a light quantity by referring to information on whether the pixel binning is on or off, the number of binning pixels n, and the like.

The light-adjusting circuit 29 also refers to light quantity ratio information to read out, from the light quantity storage portion 17, a value of LED driving currents for driving the excitation light LED 11b and the reference light LED 11c corresponding to the light quantity ratio, and controls the light quantities of the excitation light LED 11b and the reference light LED 11c through the LED driving circuit 14 using the read-out value of the LED driving currents.

The light-adjusting circuit 29 receives output signals from the CDS circuits 26a and 26b as input signals to calculate average brightness in an image of one frame (or an average luminance value in an image) by adding up the input signals for a period of, for example, several frames and dividing a resultant added value by the number of frames, or the like. The light-adjusting circuit 29 calculates a difference between the calculated average brightness and a light adjustment target value targeted by the light adjustment (i.e., a brightness target value) and outputs the resultant difference value to the LED driving circuit 14 as a light adjusting signal.

For example, if the calculated average brightness is smaller than the light adjustment target value, the light-adjusting circuit 29 outputs, to the LED driving circuit 14, a light adjusting signal of a positive difference for further increasing the light emission quantity in a present state where the LED driving circuit 14 is being driven. The LED driving circuit 14 increases a value of a present driving current in accordance with the light adjusting signal.

On the other hand, if the calculated average brightness is larger than the light adjustment target value, the light-adjusting circuit 29 outputs, to the LED driving circuit 14, a light adjusting signal of a negative difference for reducing the light emission quantity in a present state where the LED driving circuit 14 is being driven. The LED driving circuit 14 reduces a value of a present driving current in accordance with the light adjusting signal.

If it takes time to calculate an average brightness, such as in an initial state at power-on, for example, an LED driving current value of the reference light stored beforehand in memory for a light adjustment target value is read out from the memory, and the light-adjusting circuit 29 may set the value to the LED driving current of the reference light.

In the fluorescence imaging mode, if such light adjustment is performed, the light-adjusting circuit 29 refers to the information on the light quantity ratio set by the light quantity ratio setting portion 33 to perform the light adjustment control.

Although a light adjustment target value for the light-adjusting circuit 29 is typically set as a default value, from a light adjustment target value setting portion (abbreviated as target value setting portion) 35 connected with the light-adjusting circuit 29 the light adjustment target value may be variably set.

The A/D converting circuits 28a and 28b in FIG. 1 convert analog image signals into digital image signals and output the resultant signals to color balance circuits 36a and 36b.

The color balance circuit 36a includes a color separation circuit that generates image signals of R, G, and B into which the color is separated depending on the arrangement of a color separation filter. The color balance circuit 36a also includes a color balance adjustment circuit for, in the normal imaging mode, adjusting gain of amplifiers for R, G, and B (three amplifiers) to balance the colors to achieve an intensity ratio 1:1:1 among image signals of R, G, and B in order that color-separated image signals of R, G, and B may represent a picked-up image of a reference white subject as an endoscope image of the white subject.

In the fluorescence imaging mode, color balance is adjusted to achieve a predetermined intensity ratio between the gain of an amplifier for R and the gain of another amplifier that is part of the color balance circuit 36b and receives image signals of fluorescence (as input). The amplifier for R receives (as input) image signals corresponding to reflected light signals of the reference light in the color balance adjustment circuit of the color balance circuit 36a, the image signals being obtained if an image of a reference subject (emitting fluorescence) is picked up.

In the normal-light imaging mode, image signals of R, G, and B outputted from the color balance circuit 36a are stored in (synchronization) memories 38a, 38b, and 38c through a selector 37, respectively.

The image signals of R, G, and B simultaneously read out from the (synchronization) memories 38a, 38b, and 38c are subject to image processing such as γ correction in an image processing circuit 39, and then the signals are converted into analog image signals by D/A converting circuits 40a, 40b, and 40c.

The image signals of R, G, and B are outputted from the D/A converting circuits 40a, 40b, and 40c to R, G, and B channels of the monitor 5, and a display screen of the monitor 5 displays a normal endoscope image in colors.

On the other hand, in the fluorescence imaging mode, an image signal of a reflected light (reference light) and an image signal of a fluorescence are outputted for every frame from the color balance circuits 36a and 36b and stored in the synchronization memories 38a and 38b, respectively via the selector 37.

The image signal of the reflected light (reference light) and the image signal of the fluorescence simultaneously read out from the synchronization memories 38a and 38b are inputted to the image processing circuit 39. The image processing circuit 39 includes a superimposition processing portion 39a that forms superimposition processing means for performing image processing such as superimposition of image signals of fluorescence on image signals of a reflected light.

A ratio between the number of pixels of the CCD 19a and the number of pixels of the CCD 19b is set to be constant. By setting the number of pixels of the CCD 19b to, for example, about ½ to ¼ of the number of pixels of the CCD 19a, one pixel in color of the CCD 19a may correspond to one pixel in black and white of the CCD 19b.

In the case where the pixel binning is off, if there is some distance between the lenses and the living tissue, one pixel of an image of fluorescence may be superimposed on one pixel in color (for example, four pixels) of an image of a reflected light in alignment with each other. Note that if the pixel binning is turned on from the off state, depending on the number of binning pixels n, the above one pixel in color is changed to n pixels before superimposition.

An image signal of a reflected light is outputted from the image processing circuit 39 to, for example, the R channel of the monitor 5, and an image signal of fluorescence generated by the superimposition processing portion 39a is outputted to, for example, the G channel of the monitor 5. A composite image combined by superimposing the fluorescence and the reflected light on one another is displayed on the display screen of the monitor 5 in pseudo colors. A display example of the composite image is the above-mentioned illustration of FIG. 4. The timing generator 27 in FIG. 1 supplies timing signals to the A/D converting circuits 28a and 28b, the color balance circuits 36a and 36b, the selector 37, the synchronization memories 38a to 38c, the image processing circuit 39, and the D/A converting circuits 40a to 40c to cause these components to operate in synchronization with the timing signals.

A timing signal is also supplied to the LED driving circuit 14. In synchronization with the timing signal, the LED driving circuit 14 generates an LED driving current for driving a drive target of the white color light LED 11a, the excitation light LED 11b, and the reference light LED 11c to emit light.

FIGS. 5(A) and FIG. 5(B) show tables of specific examples stored in the light quantity storage portion 17 for driving the reference light LED 11c and the excitation light LED 11b.

In FIG. 5(A), in the memory constituting the light quantity storage portion 17, different memory addresses store therein values of quantities of light (illuminating light quantities) generated by the reference light LED 11c if the reference light LED 11c is driven by different LED driving currents, respectively.

In FIG. 5(B), similarly, in the memory constituting the light quantity storage portion 17, different memory addresses store therein values of quantities of light (illuminating light quantities) generated by the excitation light LED 11b if the excitation light LED 11b is driven by different LED driving currents, respectively.

For example, in the case where the light quantity ratio setting portion 33 sets a light quantity ratio between the excitation light and the reference light to 5:1 in accordance with the information on the light quantity ratio in the scope ID memory 16, if the brightness of an image calculated by the light-adjusting circuit 29 is smaller than a light adjustment target value, the light-adjusting circuit 29 increases an LED driving current value from a present value in FIG. 5(A) to an LED driving current value for the reference light LED 11c, the value depending on the difference.

The light-adjusting circuit also increases an LED driving current value for the excitation light LED 11b, the value depending on the difference, from a present LED driving current value in FIG. 5(B) so as to maintain the above-described light quantity ratio. Then, the light-adjusting circuit 29 performs light adjustment control to achieve the light adjustment target value with the brightness of the composite image displayed on the monitor 5 maintaining a predetermined light quantity ratio.

Note that a configuration example in which the CCD 19b includes the addition processing means has been described above, but addition processing means for generating, from image signals of fluorescence, addition processed signals of fluorescence in which pixels are added may be provided outside the CCD 19b, for example, in the image signal processing portion 22. If the light quantity control means controls a light quantity ratio between the excitation light and the reference light so as to maintain a predetermined light quantity ratio, not only the quantities of both the excitation light and the reference light may be controlled, but also the quantity of at least one of (or one of) the excitation light and the reference light may also be controlled.

The endoscope apparatus 1 of the present embodiment having such a configuration includes: the light source apparatus 3 as light source means (or a light source portion) including the excitation light LED 11b and the reference light LED 11c as light sources that irradiate living tissue with an excitation light for generating fluorescence and a reference light for generating a reflected light alternately; and image pickup means (or an image pickup portion) including the CCD 19a and the CCD 19b as image pickup devices having a predetermined number of pixels for picking up an image of the fluorescence generated by the irradiation of the living tissue with the excitation light and a reflected light of the reference light reflected by the living tissue.

The endoscope apparatus 1 also includes: the image signal processing portion 22 as signal processing means (or a signal processing portion) that generates image signals from signals picked up by the image pickup means; and the pixel binning portion 23b as addition processing means (or an addition processing portion) that generates, from the signals of the image pickup means obtained when the image of the fluorescence is picked up, addition processed signals of fluorescence in which pixels are added.

The endoscope apparatus 1 further includes: the light-adjusting circuit 29 as light quantity control means (or a light quantity control portion) that controls the quantity of at least one of the excitation light and the reference light so as to maintain a predetermined light quantity ratio between the quantities of the excitation light and the reference light, from the addition processed signals of the fluorescence generated by the addition processing means on the basis of the switching of the addition processing and from reflected light signals as the image signals of a reflected light generated by the signal processing means; and the superimposition processing portion 39*a* as superimposition processing means that outputs, to display means (or a display section), superimposed image signals (or composite image signals) in which the addition processed signals of the fluorescence and the reflected light signals are superimposed, with the predetermined light quantity ratio being maintained.

Figure 6A:
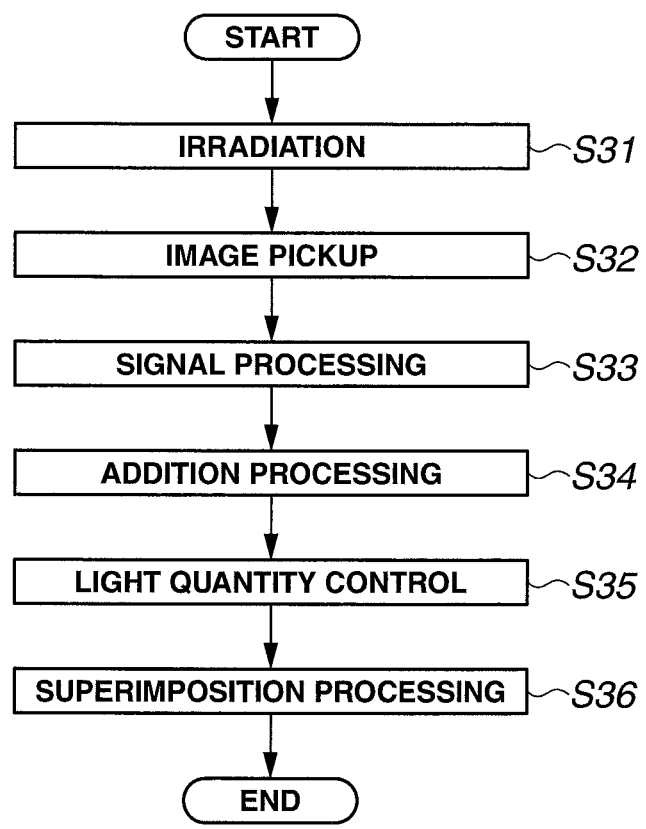
FIG. 6A is a flow chart showing an example of a process procedure of a method for controlling fluorescence imaging.

A method for controlling fluorescence imaging according to the present embodiment includes: as shown in FIG. 6A, an irradiation step S31 in which the light source apparatus 3 as a light source portion irradiates living tissue with an excitation light for generating fluorescence on the living tissue and a reference light for generating a reflected light alternately; an image pickup step S32 in which an image pickup portion including the CCDs 19*a* and 19*b* as image pickup devices having a predetermined number of pixels pick up images of the fluorescence generated if the living tissue is irradiated with the excitation light and the reflected light reflected by the living tissue from the reference light; a signal processing step S33 in which the image signal processing portion 22 as a signal processing portion generates image signals from the signals of the image picked up in the image pickup step S32; an addition processing S34 in which the pixel binning portion 23*b* as an addition processing portion generates addition processed signals of fluorescence in which addition processing is performed among a plurality of adjacent pixels from the signals, in the image pickup step S32, obtained by picking up the image of the fluorescence or from the image signals of the fluorescence generated in the signal process step S33; a light quantity control step S35 in which on the basis of the change in the number of pixels to be added in the addition processing S34, the light-adjusting circuit 29 as a light quantity control portion controls the light quantity of at least one of the excitation light and the reference light so as to maintain a predetermined light quantity ratio between the quantities of the excitation light and the reference light from the addition processed signals of the fluorescence generated in the addition processing S34 and from the reflected light signals as the image signals of a reflected light generated in the signal processing step; and a superimposition process step S36 in which the superimposition processing portion 39*a* superimposes the addition processed signals of the fluorescence and the reflected light signals and outputs, to a display portion, superimposed image signals in which the addition processed signals and the reflected light signals are superimposed, with the predetermined light quantity ratio being maintained. In the light quantity control step S35, if the number of pixels to be added is changed, the quantity of the excitation light is controlled on the basis of information on the number of pixels immediately after the change in the number of pixels.

An operation of the present embodiment will now be described. If using the endoscope 2 living tissue that is a diagnosis target in a body cavity is inspected and observed, a medication for generating fluorescence is administered to the living tissue in advance. Then, as shown in FIG. 1, the endoscope 2 is connected with the light source apparatus 3 and the video processor 4.

In the case of normal imaging, the living tissue is irradiated with a white color light by causing the white color light LED 11*a* and the excitation light LED 11*b* to simultaneously emit light. Signals picked up by the CCD 19*a* are amplified by the CD amplifier 25*a* and the CDS circuit 26*a* extracts signal components from the amplified signals. Further, the A/D converting circuit 28*a* converts the signals into digital image signals.

In addition, the signals pass through the color balance circuit 36*a* and the selector 37, and the image signals of R, G, and B are stored in the synchronization memories 38*a* to 38*c*.

The image signals of R, G, and B are read into the synchronization memories 38*a* to 38*c* and pass through the image processing circuit 39. Then, the D/A converting circuits 40*a* to 40*c* convert the signals into analog image signals of R, G, and B, and colored endoscope image is displayed on the monitor 5.

In this case, the light-adjusting circuit 29, to which an output signal from the CDS circuit 26*a* is inputted, generates a light adjusting signal. Using the generated light adjusting signal, the light-adjusting circuit 29 adjusts LED driving currents delivered to the white color light LED 11*a* and the excitation light LED 11*b* through the LED driving circuit 14 to perform light adjustment control (light quantity control) so as to maintain a light adjustment target value with which the endoscope image is displayed on the monitor 5.

An operation of the light adjustment control performed in the fluorescence imaging mode will now be described with reference to FIG. 6B.

As shown in FIG. 6B, the light quantity ratio setting portion 33 sets the light quantity ratio between the excitation light and the reference light in response to a manual direct input of the light quantity ratio from the input portion 34 (S1) or a light quantity ratio input read out from the scope ID memory 16 (S2).

In FIG. 6B, a setting example of the light quantity ratio between the excitation light and the reference light being 5:1 (S3) is described. The information on the light quantity ratio is inputted to the light-adjusting circuit 29, and the light-adjusting circuit 29 sets a reference light LED driving current on the basis of the light adjustment target value (S4).

The LED driving circuit 14 sets a reference light LED driving current on the basis of the light adjustment target value (S5).

The light-adjusting circuit 29 also reads out an excitation light LED driving current that achieves the light quantity ratio from the light quantity storage portion 17 to control a driving current for the LED driving circuit 14 (S6).

The LED driving circuit 14 sets the LED driving current for the reference light LED 11*c* and also sets the LED driving current for the excitation light LED 11*b* (S7).

Then, the LED driving circuit 14 causes the reference light LED 11*c* and the excitation light LED 11*b* to emit lights alternately using the reference light LED driving current and the excitation light LED driving current (S8).

The light-adjusting circuit 29 also performs the light adjustment control to attain an endoscope image having the brightness of the light adjustment target value by calculating the brightness of an image from the output signals of the CDS circuits 26*a* and 26*b* and controlling the driving current for the LED driving circuit 14 depending on the difference from the light adjustment target value (S9).

In FIG. 6B, the case where the function of pixel binning, which is pixel addition, is turned off has been explained. In the fluorescence imaging mode, the light adjustment control may also be performed with the pixel binning, the pixel addition, being turned on as shown in FIG. 7.

In step S11, the first step in FIG. 7, the light-adjusting circuit 29 controls the light quantities of the reference light LED 11*c* and the excitation light LED 11*b* with the pixel addition (pixel binning) turned off.

As shown in step S12, the light-adjusting circuit 29 monitors the pixel binning on/off operation performed by the binning setting portion 32.

If an operator feels that the brightness of an image displayed on the monitor 5 is low in the pixel binning off state, the operator may turn on the pixel binning by the binning setting portion 32. Alternately, if the operator does not desire to turn on the pixel binning, the operator may keep the pixel binning off.

The light-adjusting circuit 29 determines whether or not the pixel binning is on in step S13. If a determination result in step S13 is that the pixel binning is off, the light-adjusting circuit 29 maintains a present LED driving current as shown in step S14.

In step S15, the next step, the light-adjusting circuit 29 generates light adjusting signals on the basis of an obtained fluorescence image (a superimposed composite image).

As shown in step S16, the next step, the light-adjusting circuit 29 controls the light quantities of the respective LEDs (the excitation light LED 11b and the reference light LED 11c) through the LED driving circuit 14 on the basis of the generated light adjusting signals. After the process in step S16, the method returns to the process in step S12.

On the other hand, if a determination result in step S13 is that the pixel binning is on, as shown in step S17, the light-adjusting circuit 29 switches a present (before pixel binning switching) excitation light LED driving current down to 1/n based on the number of binning pixels n. This process restrains stepwise sudden change of the fluorescence intensity that is before the switching since the pixel binning stepwisely improves the sensitivity of the CCD 19b by the number of binning pixels n.

In step S18, the next step, the light-adjusting circuit 29 generates light adjusting signals on the basis of the brightness of a fluorescence image (a superimposed composite image) obtained after the switching in step S17. As shown in step S19, the next step, the light-adjusting circuit 29 controls the light quantity of each LED through the LED driving circuit 14 on the basis of the generated light adjusting signals.

As shown in steps S17 to S19, the light quantity control by the pixel binning can improve the sensitivity of the CCD 19b by the number of binning pixels n, and the operator is allowed to carry out a diagnosis with a fluorescence image (a superimposed composite image) that is easy to use for the purpose of diagnosis.

Also, if the pixel binning is switched from the off state to the on state as described above, the sensitivity of the CCD 19b is stepwisely increased, but by reducing an LED driving current for driving the excitation light LED 11b to 11n immediately after the switching, stepwise change in the brightness of part of the fluorescence image can be effectively prevented before and after the switching (between frames before and after the switching).

As hereinbefore described, according to the present embodiment, the endoscope apparatus 1 can be realized which is applicable to the case where pixel addition processing is performed and can display an image in which image signals of fluorescence and image signals of a reflected light are superimposed, without changing the balance between both the images. In particular, advantageously, a composite image in which both images are superimposed on one another in pseudo color may be displayed without changing the color balance.

Note that in the fluorescence imaging mode, if light quantity control is performed with the pixel binning on as shown in steps S17 to S19 of FIG. 7, the number of binning pixels n may also be switched (changed).

FIG. 8 shows an operation in which the number of binning pixels n is switched. After the process in step S19 of FIG. 7, the light-adjusting circuit 29 monitors whether or not the number of binning pixels n has been changed by the switching of the binning setting portion 32 and determines whether or not the number of binning pixels n has been changed (switched) to m (n≠m) as shown in step S21.

If a determination result is that the number is not changed, the method returns to the process in step S18, and the same operation is performed.

On the other hand, if the number of binning pixels n has been changed to m, an excitation light LED driving current before the switching is switched to n/m in step S22.

After the process in step S22, in the same manner as the processes in steps S18 and S19 of FIG. 7, in step S23, the light-adjusting circuit 29 generates light adjusting signals on the basis of the fluorescence image (the superimposed composite image) obtained after the changing (switching). In step S24, the next step, the light-adjusting circuit 29 performs the light quantity control of each LED on the basis of the light adjusting signals.

By performing such control, even if the number of binning pixels n is changed, light quantity control can be properly performed to obtain a fluorescence image that is easy to use for the purpose of diagnosis.

Note that in the fluorescence imaging mode, pixel binning automatic adjustment mode may be provided for automatically switching on and off the pixel binning by the binning setting portion 32 and for, if the pixel binning is on, switching the number of binning pixels.

In this case, as shown in FIG. 9A, an upper-limit value of an LED driving current corresponding to an allowable maximum light emission quantity of the excitation light (an upper-limit value of the quantity of the excitation light) from the excitation light LED 11b is set to a threshold, and thereby the threshold is inputted to the light-adjusting circuit 29 from a threshold setting portion 51. If the light quantity control is performed through the LED driving circuit 14, the light-adjusting circuit 29 refers to the threshold and performs the light quantity control with the LED driving current for the excitation light LED 11b being not higher than the value.

Figure 9B:
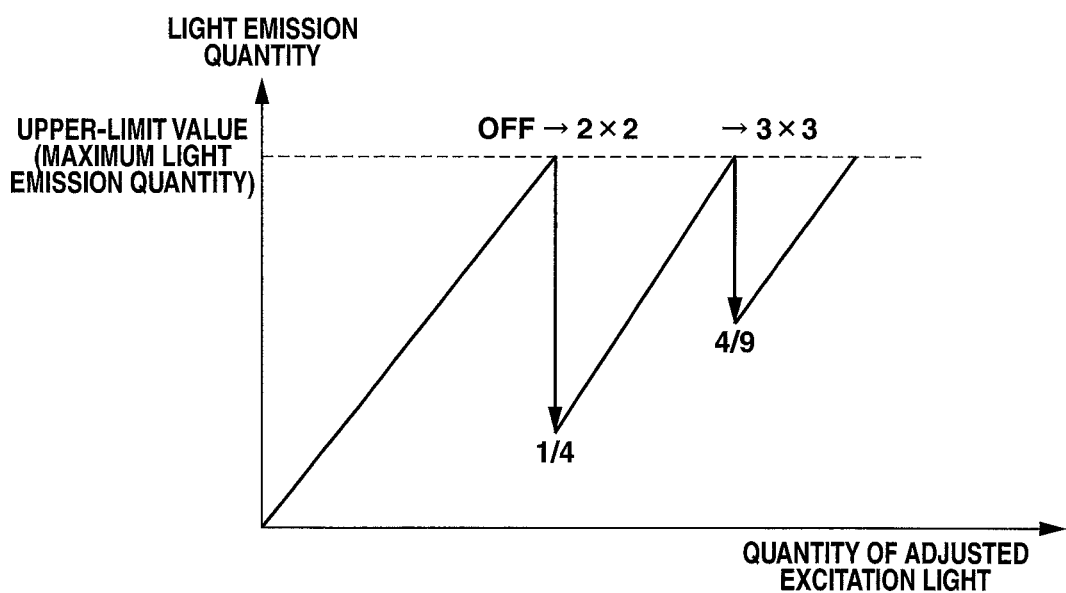
FIG. 9B is an explanatory diagram of an operation of light quantity control performed by the light-adjusting circuit adjusting the number of binning pixels to be automatically added at an upper-limit value of excitation light.

FIG. 9B shows an operation if the pixel binning automatic adjustment mode is set. In FIG. 9B, a vertical axis indicates light emission quantity of the excitation light and a horizontal axis indicates change with respect to time in quantity of the excitation light adjusted by the light adjustment control from the pixel binning off state.

As described above, since an upper-limit value of the excitation light is set to a threshold, light quantity control is performed so that the quantity of the excitation light does not exceed the upper-limit value. First, the light quantity control is performed with the pixel binning off, and the light quantity control is performed by the light-adjusting circuit 29.

Once the quantity of the excitation light reaches the upper-limit value, the light-adjusting circuit 29 turns on the pixel binning from the off state. At this time, the light-adjusting circuit 29 adopts pixel binning with a minimum number of binning pixels, four, that is, 2×2 and switches the quantity of the excitation light to ¼.

The light-adjusting circuit 29 performs the light quantity control in this state. If the quantity of the excitation light in the light quantity control also reaches the upper-limit value, the light-adjusting circuit 29 adopts pixel binning with a second number of binning pixels, 3×3 and switches the quantity of the excitation light to 4/9. In this way, the sensitivity is improved by switching the number of binning pixels in stages.

If the sensitivity is improved by switching the number of binning pixels in stages as previously described, the quantity of the excitation light is reduced by the number of binning pixels so as to prevent fluorescence image part from becoming suddenly bright.

In FIG. 9B, the case where a fluorescence image becomes dark with time has been explained, but if fluorescence image part becomes bright, the number of binning pixels is automatically switched to be reduced so as to prevent the brightness of the fluorescence image part from being changed before and after the switching.

If the pixel binning automatic adjustment mode is set as shown in FIG. 9B, without the operator manually switching the number of binning pixels, a fluorescence image having proper brightness that is easy to use for the purpose of diagnosis is allowed to be automatically obtained.

Modification of First Embodiment

Figure 10:
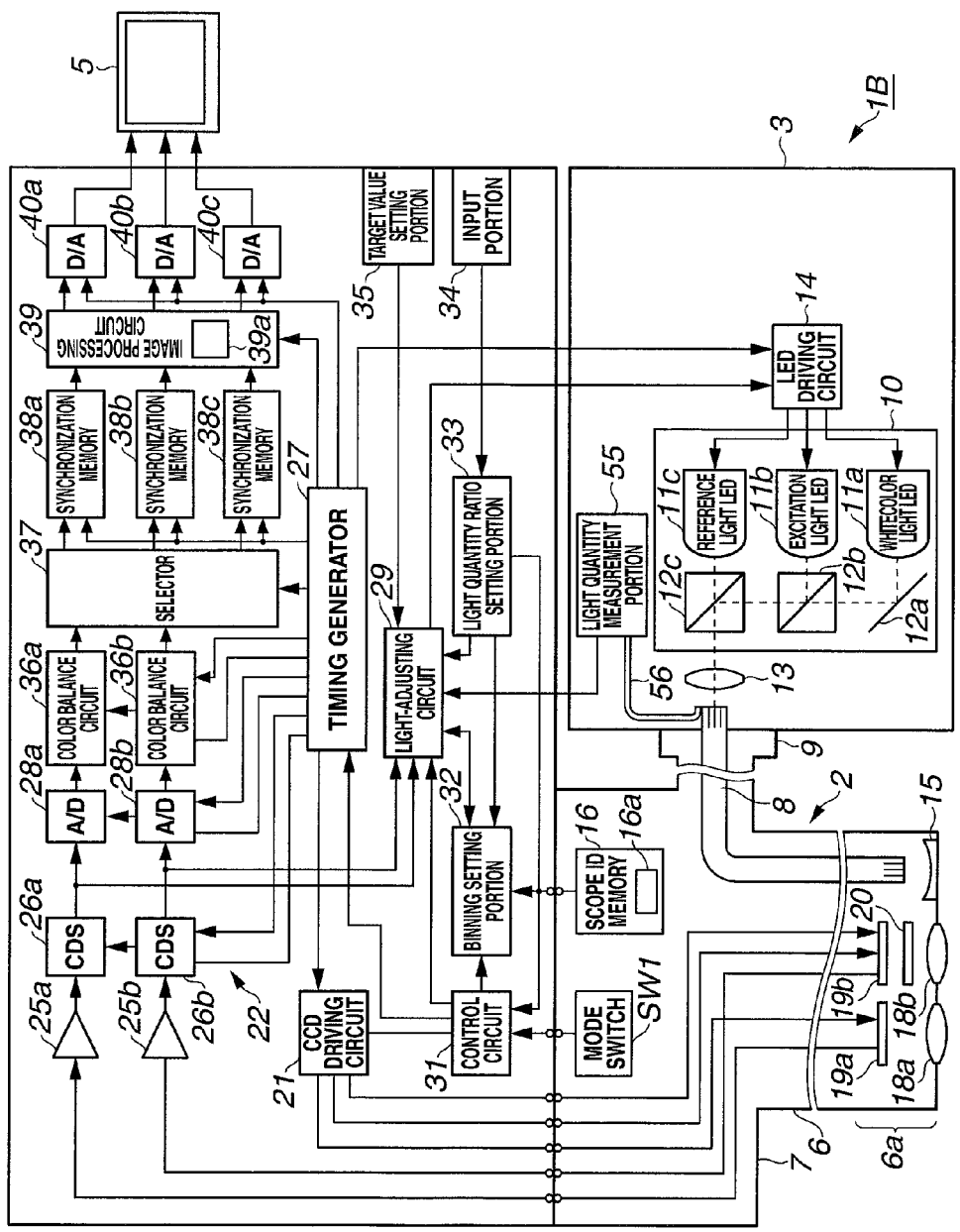
FIG. 10 is a diagram showing an entire configuration of an endoscope apparatus according to a modification of the first embodiment.

FIG. 10 shows an endoscope apparatus 1B of a modification of the first embodiment. The endoscope apparatus 1B has a configuration in which the light quantity storage portion 17 is removed from and a light quantity measurement portion 55 is provided in the endoscope apparatus 1 in FIG. 1.

The light quantity measurement portion 55 measures the quantity of an excitation light from the excitation light LED 11$b$ and the quantity of a reference light from the reference light LED 11$c$, from light transmitted through a fiber 56 that receives part of light supplied from, for example, the condenser lens 13 to an incident end face of the light guide 8.

The quantity of the excitation light and the quantity of the reference light by the reference light LED 11$c$ which are measured by the light quantity measurement portion 55 are inputted to the light-adjusting circuit 29. The light-adjusting circuit 29 refers to the quantities of the excitation light and the reference light measured by the light quantity measurement portion 51 to control the quantities of the excitation light and the reference light through the LED driving circuit 14 on the basis of a light adjusting signal.

Note that without using the fiber 56, a mirror that reflects a sufficiently small ratio of light compared with the quantity of transmission light may be disposed between the condenser lens 13 and the incident end face of the light guide 8. The reflected light may be received by a light quantity detecting sensor and the light quantity measurement portion 55 may measure, from signals detected by the light quantity detecting sensor, the quantity of the excitation light from the excitation light LED 11$b$ and the quantity of the reference light from the reference light LED 11$c$.

The other components are the same as those in FIG. 1.

In the present modification, the light-adjusting circuit 29 refers to the quantity of the excitation light measured by the light quantity measurement portion 55 and the quantity of the reference light from the reference light LED 11$c$ to control the quantities of the excitation light and the reference light.

An operation of the present modification is similar to the operation of the first embodiment. In the operation of the first embodiment, shown in FIG. 6B, the process S6 is changed to: "set an LED driving current for the excitation light LED 11$b$ so that the quantity of the excitation light measured by the light quantity measurement portion 55 achieves the light quantity ratio 5:1 between the excitation light and the reference light."

Also, in an operation corresponding to FIG. 7, the process in step S17 is replaced by "switch a present (before pixel binning switching) quantity of the excitation light to 1/n based on the number of binning pixels n."

The present modification has a similar effect to that of the first embodiment.

Second Embodiment

Next, a second embodiment of the present invention will be described. The present embodiment has a configuration in which for example, the image processing circuit 39 in FIG. 1 or FIG. 10 provides therein an image addition processing circuit 39$b$ that adds about two to four frames of images adjacent on a time-series basis for only fluorescence image components.

Figure 11:
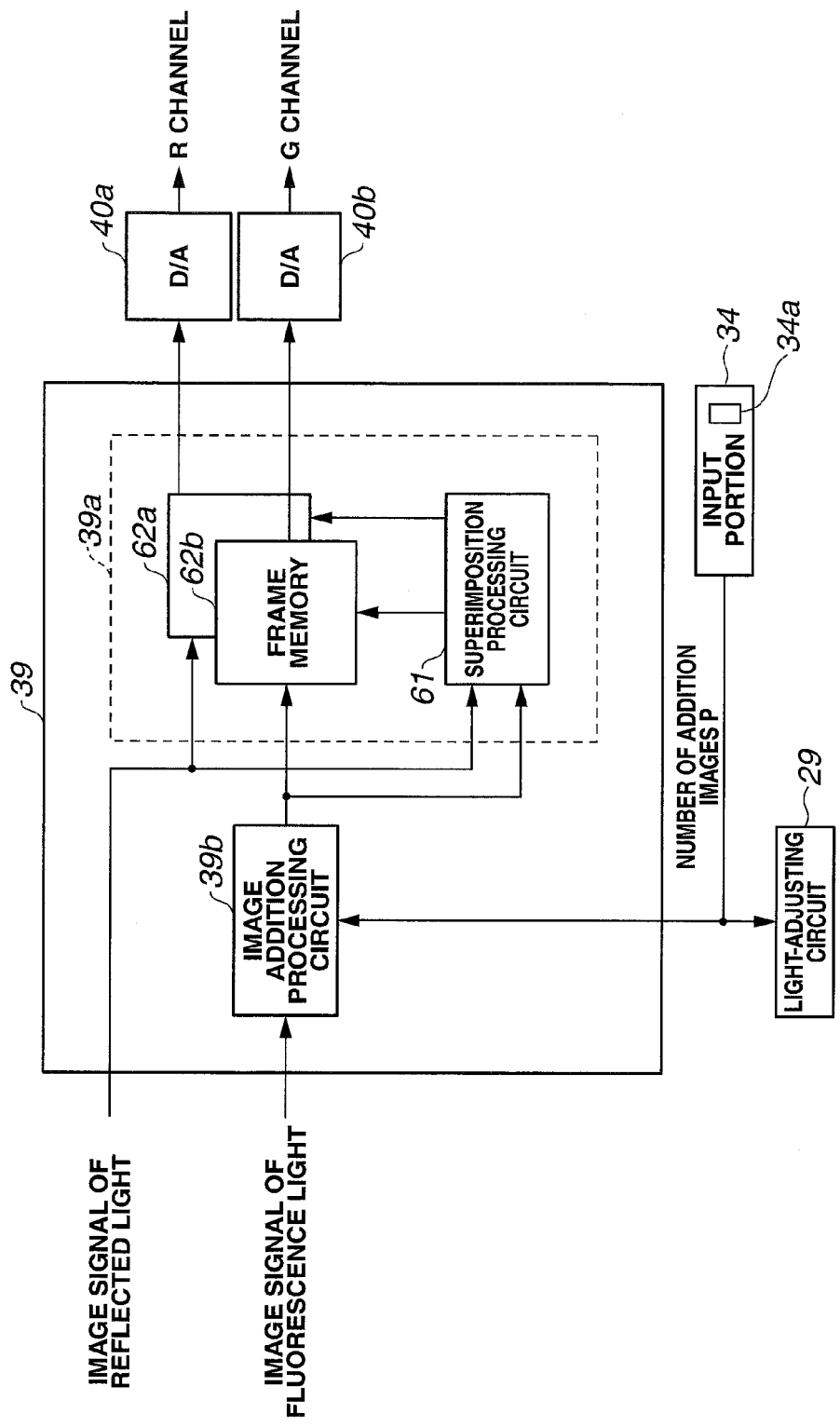
FIG. 11 is a block diagram showing a configuration of an image processing circuit in which an image addition processing circuit is provided for addition processing between images in a second embodiment of the present invention.

FIG. 11 shows the image processing circuit 39 in the present embodiment. As shown in FIG. 11, fluorescence image signals are inputted to the image addition processing circuit 39$b$. The image addition processing circuit 39$b$ outputs, to the superimposition processing portion 39$a$, image addition processed signals in which images of a plurality of frames adjacent on a time-series basis are added.

A superimposition processing circuit 61 of the superimposition processing portion 39$a$ also receives image signals of a reflected light (as input). The superimposition processing circuit 61 generates image signals of a composite image (also referred to as composite image signals) as superimposition image signals in which the image addition processed signals and the image signals of the reflected light are superimposed on one another.

Image components of a reflected light that form image signals of a composite image are stored in a first frame memory 62$a$, and the other image addition processed signals are stored in a second frame memory 62$b$.

The respective image signals in the frame memories 62$a$ and 62$b$ are outputted to the D/A converting circuits 40$a$ and 40$b$, where the signals are each converted into analog image signals. Then, the resultant signals are outputted to, for example, the R and the G channels of the monitor 5 and displayed on the monitor 5 in pseudo colors.

Note that the number of a plurality of frames of images (abbreviated as the number of addition images) P which are added from, for example, the input portion 34 may be inputted to the image addition processing circuit 39$b$. The image addition processing circuit 39$b$ performs image addition processing with the inputted number of addition images P. The input portion 34 includes a setting portion 34$a$ that sets the number of addition images P.

A luminance level of image signals of a fluorescence image in image signals of a composite image outputted by the image addition processing circuit 39$b$ to the monitor 5 via the superimposition processing portion 39$a$ is P times higher than that in the case where the operation of the image addition processing circuit 39$b$ is turned off.

Since a luminance level of image signals of a fluorescence image inputted from the CDS circuit 26$b$ to the light-adjusting circuit 29 does not reflect the fact, in order to reflect it, the input portion 34 also outputs the number of addition images P to the light-adjusting circuit 29 and increases the signal level inputted from the CDS circuit 28$b$ to the light-adjusting circuit 29 P fold to generate light adjusting signals.

If the image addition processing is switched from the off state to the on state, the light-adjusting circuit 29 switches (changes) the quantity of a reference light or an LED driving current to 1/P from that before the switching to that after the switching.

If image addition is performed in this way, i.e., similarly to pixel addition, the light-adjusting circuit 29 performs light quantity control so as not to change the color balance of a composite image due to sudden increase in only fluorescence image components. By performing image addition in addition to pixel addition, even if the brightness of a fluorescence image is insufficient, a problem of the insufficiency can be solved or reduced.

The other components and operations are the same as those in the first embodiment.

Note that the image processing circuit 39 shown in FIG. 11 is illustrated with a configuration in the fluorescence imaging mode. In the normal imaging mode, the configuration of the image processing circuit 39 is similar to that in the first embodiment.

In the fluorescence imaging mode, the present embodiment has a function of image addition processing in addition to the function of pixel addition processing by pixel binning as in the first embodiment.

Thus, the present embodiment has the effect of the operation of the first embodiment and can further provide a fluorescence image that is easy to use for the purpose of diagnosis by the image addition processing in the fluorescence imaging mode.

For example, since the resolution of fluorescence image part is lowered if the number of binning pixels n of pixel binning is too large, the operator sets an upper-limit value of, for example, the number of binning pixels n. If the quantity of an excitation light is insufficient even in the set upper-limit value, the operator increases the number of addition images P in image addition processing. Thereby, the resolution of fluorescence image part can be prevented from being lowered and a required quantity of an excitation light can be ensured.

Figure 12:
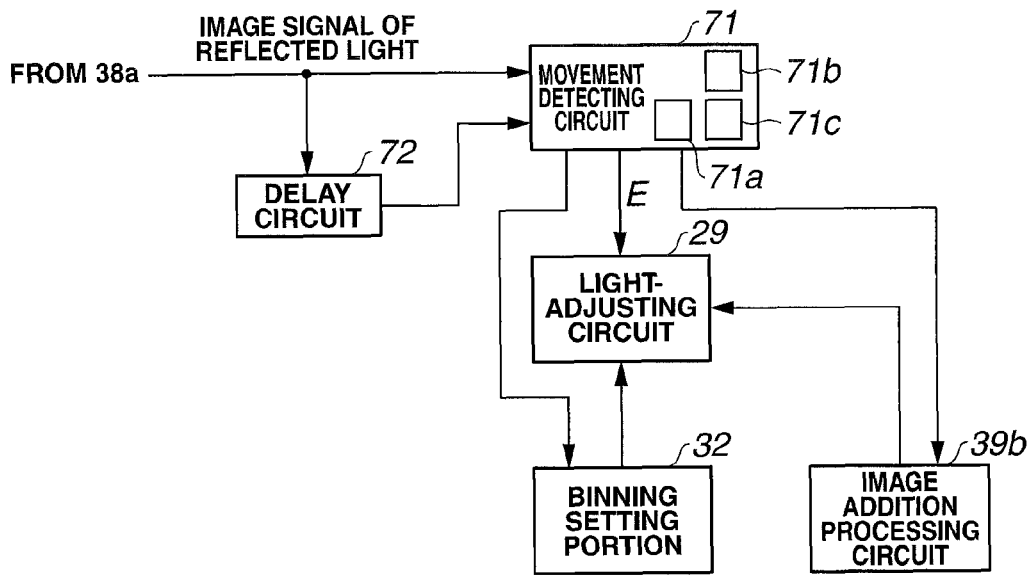
FIG. 12 is a block diagram showing a configuration of a movement detecting circuit that detects the movement between images and surrounding circuits.
Figure 13:
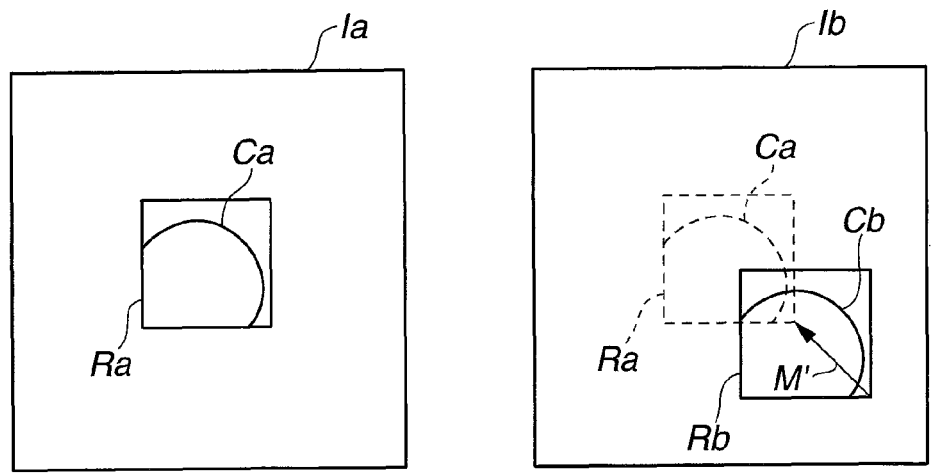
FIG. 13 is an explanatory diagram showing the detection of a movement amount from images of two temporally different frames.

As shown in FIG. 12, a movement detecting circuit 71 may be provided. The movement detecting circuit 71 detects a temporal movement amount from, for example, image signals of a reflected light that form a superimposed composite image. On the basis of detection signals of the movement amount from the movement detecting circuit 71, the number of addition images P and/or a range of the number of binning pixels n may be restrained. FIG. 13 shows how the movement detecting circuit 71 detects a movement amount from two images Ia and Ib.

In a configuration example of FIG. 12, for example, image signals of a reflected light outputted from the synchronization memory 38a and image signals delayed by one to several frames through a delay circuit 72 are inputted to the movement detecting circuit 71. As shown in FIG. 13, the movement detecting circuit 7 detects a movement amount M' that indicates the movement of a characteristic part or a criterion part Ca from a characteristic part or a criterion part Cb. The part Ca is, for example, an outline extracted from any range Ra set in the former image Ia, and the part Cb is in a range Pb included in the latter image Ib. The movement detecting circuit 71 then calculates (or detects) an average movement amount M among frames from a detection result. Note that if the images Ia and Ib are temporally different from each other by Q frames, M=M'/Q.

The movement detecting circuit 71 also calculates an evaluated number of pixels E obtained by evaluating the number of pixels to which the calculated movement amount M corresponds among frames in the CCD 19b for picking up an image of fluorescence. The movement detecting circuit 71 then outputs the evaluated number of pixels E to the light-adjusting circuit 29, the binning setting portion 32, and the image addition processing circuit 39b. Thus, the movement detecting circuit 71 includes an evaluated number-of-pixels calculating portion 71a that calculates the evaluated number of pixels E obtained by evaluating the number of pixels to which the movement amount M corresponds for one frame. The movement detecting circuit 71 also includes a first control circuit 71b that uses the evaluated number of pixels E to control an upper-limit value of the number of addition images in the addition performed by the image addition processing circuit 39b and a second control circuit 71c that restrains an upper-limit value of the pixel number n of binning performed by the binning setting portion 32.

For example, if a value of the evaluated number of pixels E is small, that is, the movement amount M is small, the movement detecting circuit 71 causes an upper-limit value of the number of addition images in the addition performed by the image addition processing circuit 39b to be set at a larger value and causes an upper-limit value of the number of binning pixels n to be restrained for the binning setting portion 32.

The light-adjusting circuit 29 performs light quantity control in such a control state.

On the other hand, if a value of the evaluated number of pixels E is large, that is, the movement amount M is large, the movement detecting circuit 71 causes an upper-limit value of the number of addition images in the addition performed by the image addition processing circuit 39b to be lowered and allows an upper-limit value of the number of binning pixels n to be set at a larger value for the binning setting portion 32. The light-adjusting circuit 29 performs light quantity control in such a control state.

Note that when an upper-limit value of the number of binning pixels n is restrained using the evaluated number of pixels E, because a pixel region size causing blur for every frame is E×E, letting Ub be an upper-limit value, the number of binning pixels n may be set to meet the condition Ub≤E×E. On the other hand, if it is assumed that an upper-limit value of the number of addition images is Ui, letting Tm be a threshold of the number of pixels with which an outline of moving part is recognized as obviously discontinuous within one frame, the number of addition images may be set to meet the condition Ui≤Tm/E.

Note that the light-adjusting circuit 29, to which the evaluated number of pixels E calculated by the movement detecting circuit 71 (or the evaluated number-of-pixels calculating portion 71a thereof) is inputted, may control the number of addition images from the image addition processing circuit 39b and control the number of binning pixels n for the binning setting portion 32.

If part with less movement is observed, such control by the light-adjusting circuit 29 allows the number of binning pixels n to be restrained and image addition processing to cover the sensitivity insufficient at that number of binning pixels n.

In this way, a resolution of fluorescence image part can be prevented from lowering and observation can be accomplished with the color balance being unchanged. Meanwhile, if movement is significant, the sensitivity can be improved by pixel binning to generate an image being easy to use for the purpose of diagnosis by following the movement.

In the foregoing configuration, the case where image signals of a reflected light are used has been described, but image signals of fluorescence may also be used to detect movement.

Note that image signals of a composite image in which image signals of fluorescence and image signals of a reflected light are superimposed are not limited to image signals of a fluorescence image and red (R) components, and may be image signals of G components or B components (image signals in two pseudo colors). Alternatively, image signals in three pseudo colors may be generated from a plurality of image signals.

An embodiment constituted by partially combining the foregoing embodiments with each other shall fall within the scope of the present invention.

What is claimed is:

1. An endoscope apparatus comprising:
a light source portion including light sources that irradiate living tissue with an excitation light for generating fluorescence and a reference light for generating a reflected light alternately;
an image pickup portion including image pickup devices having a predetermined number of pixels for picking up images of the fluorescence generated by the irradiation of the living tissue with the excitation light and a reflected light of the reference light reflected by the living tissue;
a signal processing portion that generates image signals from signals picked up by the image pickup portion;
a light quantity ratio setting portion that sets a light quantity ratio between the excitation light and the reference light;
an addition processing portion that generates, from fluorescence signals obtained when the image of the fluorescence is picked up or the image signals of the fluorescence generated by the signal processing portion, addition processed signals of fluorescence in which a plurality of adjacent pixels are added;
a light quantity control portion that, when the addition processed signals are generated by the addition processing portion, reduces a driving current for excitation light in the light source portion according to the number of addition processed pixels, generates a light adjusting signal on the basis of brightnesses of the addition processed signals of the fluorescence and reflected light signals as the image signals of the reflected light, and controls a quantity of at least one of the excitation light and the reference light so as to maintain a predetermined light quantity ratio between the excitation light and the reference light set by the light quantity ratio setting portion on the basis of the light adjusting signal; and
a superimposition processing portion that outputs, to a display portion, superimposed image signals in which the addition processed signals of the fluorescence and the reflected light signals are superimposed, with the predetermined light quantity ratio being maintained in the light quantity control portion.

2. The endoscope apparatus according to claim 1, further comprising a number-of-pixels setting portion that sets a number of pixels to be added by the addition processing portion to generate a pixel signal of one pixel from a plurality of pixels, wherein if the number of pixels to be added is set, the light quantity control portion controls the quantity of the excitation light on the basis of information on the number of pixels immediately after the number of pixels is set.

3. The endoscope apparatus according to claim 2, wherein
the light quantity control portion generates the light adjusting signal to achieve predetermined brightness of the superimposed image signals in which the addition processed signals of the fluorescence and the reflected light signals are superimposed, with the predetermined light quantity ratio being maintained, and
if it is determined that the quantity of the excitation light generated by the light source portion needs a value higher than an upper-limit value of the quantity of the excitation light in order to set the brightness of the superimposed image signals to the predetermined brightness, the addition processing portion is controlled to increase a present number of addition pixels J to a number of pixels K and change the quantity of the excitation light to J/K immediately after the number of pixels is increased.

4. The endoscope apparatus according to claim 3, further comprising an image addition processing portion that performs addition processing of the image signals of the fluorescence among a plurality of (P) images picked up on a time-series basis, wherein the light quantity control portion controls the light quantity of the excitation light depending on an operation of the image addition processing portion.

5. The endoscope apparatus according to claim 4, further comprising a movement detection portion that detects a movement amount for one frame from images among temporally different frames in the superimposed image signals, wherein depending on the detected movement amount value, the movement detection portion restrains an upper-limit value of the number of pixels added by the addition processing portion and an upper-limit value of the number of a plurality of (P) images added by the image addition processing portion.

6. The endoscope apparatus according to claim 5, wherein the movement detection portion further includes an evaluated number-of-pixels calculating portion that calculates from the movement amount value an evaluated number of pixels corresponding to the number of pixels moving for one frame, and if the evaluated number of pixels is a large value, the movement detection portion restrains an upper-limit value of the plurality (P) with which the image addition processing portion performs the addition processing, and if the evaluated number of pixels is a small value, the movement detection portion restrains an upper-limit value of the number of pixels added by the addition processing portion.

7. The endoscope apparatus according to claim 3, further comprising a movement detection portion that detects a movement amount for one frame from images among temporally different frames in the superimposed image signals, wherein depending on the detected movement amount value, the movement detection portion restrains an upper-limit value of the number of pixels added by the addition processing portion.

8. The endoscope apparatus according to claim 7, wherein the movement detection portion further includes an evaluated number-of-pixels calculating portion that calculates from the movement amount value an evaluated number of pixels corresponding to the number of pixels moving for one frame.

9. The endoscope apparatus according to claim 3, further comprising an image addition processing portion that performs addition processing on the image signals of the fluorescence among a plurality of (P) images picked up on a time-series basis, wherein in response to changing of an operation of the image addition processing portion from an off state to an on state, the light quantity control portion controls a quantity of the excitation light to 1/P of a quantity of light in the off state.

10. The endoscope apparatus according to claim 2, wherein the signal processing portion superimposes the addition processed signals of the fluorescence and the reflected light signals on one another to generate image signals in pseudo color as the superimposed image signals.

11. The endoscope apparatus according to claim 1, wherein
the light source portion includes a mode switch that switches between a fluorescence imaging mode in which living tissue is irradiated with the excitation light and the reference light and a normal imaging mode in which the living tissue is irradiated with a white color light, and
if the normal imaging mode is selected, the signal processing portion generates colored image signals from signals picked up by the image pickup portion and outputs the colored image signals to the display portion.

12. A method for operating an endoscope apparatus comprising a light source portion including light sources that irradiate living tissue with an excitation light for generating fluorescence and a reference light for generating a reflected light alternately, and an image pickup portion including image pickup devices having a predetermined number of pixels for picking up images of the fluorescence generated by the irradiation of the living tissue with the excitation light and a reflected light of the reference light reflected by the living tissue, the method comprising:

a signal processing step in which a signal processing portion generates image signals from obtained fluorescence signals and reflected light signals reflected by living tissue;

a light quantity ratio setting step in which a light quantity ratio setting portion sets a light quantity ratio between the excitation light and the reference light;

a pixel addition processing step in which a pixel addition processing portion generates addition processed signals of fluorescence obtained by addition processing among a plurality of adjacent pixels from the fluorescence signals or the image signals of the fluorescence generated in the signal processing step;

a light quantity control step in which, when the addition processed signals are generated in the pixel addition processing step, a light quantity control portion reduces a driving current for excitation light in the light source portion according to the number of addition processed pixels, generates a light adjusting signal on the basis of brightnesses of the addition processed signals of the fluorescence and reflected light signals as the image signals of the reflected light, and controls a quantity of at least one of the excitation light and the reference light so as to maintain a predetermined light quantity ratio between the excitation light and the reference light set by the light quantity ratio setting portion on the basis of the light adjusting signal; and a superimposition signal generating step in which a superimposition processing portion generates superimposed image signals in which the addition processed signals of the fluorescence and the reflected light signals are superimposed, with the predetermined light quantity ratio being maintained in the light quantity control step.

13. The method for operating an endoscope apparatus according to claim 12, wherein if the light quantity control step determines that a quantity of an excitation light by which the light source portion generates the fluorescence needs a value higher than an upper-limit value of the quantity of the excitation light in order to achieve predetermined brightness, the step increases a number of pixels J in present addition processing to a larger number of pixels K in the pixel addition processing step and generates a light adjusting signal for changing the quantity of the excitation light to J/K immediately after the number of pixels is increased.

14. The method for operating an endoscope apparatus according to claim 13, further comprising an image addition processing step in which an image addition processing portion performs addition processing of the image signals of the fluorescence among a plurality of (P) images picked up on a time-series basis, wherein the light quantity control step generates a light adjusting signal for controlling the light quantity of the excitation light depending on an operation in the image addition processing step.

15. The method for operating an endoscope apparatus according to claim 13, further comprising a movement detecting step in which a movement detection portion detects a movement amount for one frame from images among temporally different frames in the superimposed image signals, wherein depending on the detected movement amount value, the movement detecting step restrains an upper-limit value of the number of pixels added in the pixel addition processing step.

16. The method for operating an endoscope apparatus according to claim 14, further comprising a movement detecting step in which a movement detection portion detects a movement amount for one frame from images among temporally different frames in the superimposed image signals, wherein depending on the detected movement amount value, the movement detecting step restrains an upper-limit value of the number of pixels added in the pixel addition processing step and an upper-limit value of the number of a plurality of (P) images added in the image addition processing step.

* * * * *